United States Patent [19]

Kleiner

[11] 4,088,677

[45] May 9, 1978

[54] CARBOXYPHENYL-ALKYLPHOSPHINIC ACIDS, THEIR ESTERS AND PROCESS FOR THEIR PREPARATION

[75] Inventor: Hans-Jerg Kleiner, Bad Soden am Taunus, Germany

[73] Assignee: Hoechst Aktiengesellschaft, Frankfurt am Main, Germany

[21] Appl. No.: 757,504

[22] Filed: Jan. 7, 1977

Related U.S. Application Data

[60] Continuation of Ser. No. 658,882, Feb. 18, 1976, abandoned, which is a division of Ser. No. 505,630, Sep. 13, 1974, Pat. No. 3,974,243.

[30] Foreign Application Priority Data

Sep. 17, 1973 Germany .............................. 2346657

[51] Int. Cl.$^2$ .......................... C07F 9/30; C07C 69/76
[52] U.S. Cl. .............. 260/502.4 R; 560/103; 560/112
[58] Field of Search ............. 260/502.4 R; 560/103, 560/112

[56] References Cited

U.S. PATENT DOCUMENTS

| 3,052,653 | 9/1962 | Iannicelli | 260/502.4 R |
| 3,178,469 | 4/1965 | Fields | 260/502.4 R |
| 3,493,639 | 2/1970 | Tavs | 260/502.5 |

FOREIGN PATENT DOCUMENTS 866,042  4/1961  United Kingdom .......... 260/502.4 R

OTHER PUBLICATIONS

Dougherty et al, "Chem. Abstracts", vol. 68, (1968), p. 10621, 110020t.
Merck Index, 6th ed. (1952), p. 228.

*Primary Examiner*—Joseph E. Evans
*Attorney, Agent, or Firm*—Curtis, Morris & Safford

[57] ABSTRACT

Carboxyphenyl-alkylphosphinic acids and the esters thereof corresponding to the formula I

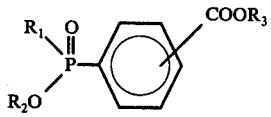

where $R_1$ is alkyl having from 1 to 4 carbon atoms, $R_2$ and $R_3$, independently, each are hydrogen, alkyl having from 1 to 12 carbon atoms, or oxyalkyl HO-$(CH_2)_n$—CHR—, $n$ being 1 to 3 and R hydrogen or alkyl having from 1 to 4 carbon atoms, and a process for the preparation of these compounds.

5 Claims, No Drawings

CARBOXYPHENYL-ALKYLPHOSPHINIC ACIDS, THEIR ESTERS AND PROCESS FOR THEIR PREPARATION

This is a continuation of application Ser. No. 658,882, filed Feb. 18, 1976 and now abandoned, which application is a divisional application of Ser. No. 505,630 filed Sept. 13, 1974 and now U.S. Pat. No. 3,974,243.

p-carboxyphenyl-phenylphosphinic acid is already known and has been prepared by L. D. Quinn et al. with unsatisfactory yields (L. D. Quinn et al., J. org. Chem. 27, 4120 (1962)):

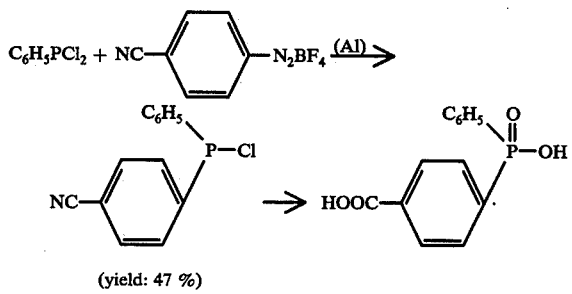

(yield: 47 %)

In this process, the reaction product of phenyldichlorophosphine and p-cyanophenyl-diazonium-tetrafluoroborate has to be subjected to a reduction with aluminum in order to obtain the p-cyanophenyl-phenylchlorophosphine. The yield is 47% of the theoretical yield. This process can be carried out only with difficulty on a large scale, and the formation of large amounts of fluorine containing waste secondary products creates the problem of the pollution-free destruction thereof.

Furthermore, it is known from British Pat. No. 1,200,273 (corresponding to U.S. Pat. No. 3,493,639) and from German Offenlegungsschrift No. 2,118,223 (corresponding to U.S. Pat. No. 3,705,214) to react phosphorus compounds of the formula R'R"P-OR, where R is alkyl, with optionally substituted phenyl halides to obtain compounds of the formula R'R"P(O)-phenyl (substituted). Carboxyphenyl-alkylphosphinic acids, or their esters or diesters, however, are neither described in these patents, nor even cited, not to mention their preparation.

The present invention now provides carboxyphenyl-alkylphosphinic acids and the esters thereof corresponding to the formula I

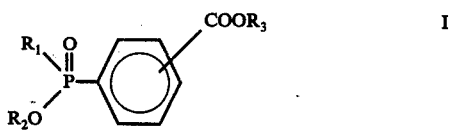

where $R_1$ is alkyl having from 1 to 4, preferably from 1 to 2 carbon atoms, $R_2$ and $R_3$, independently, each are hydrogen, alkyl having from 1 to 12, preferably from 1 to 4, especially 1 or 2 carbon atoms, or oxyalkyl HO-$(CH_2)_n$-CHR-, $n$ being 1 to 3 and R hydrogen or alkyl having from 1 to 4 carbon atoms. Preferably, $R_2 = R_3 =$ H or $CH_3$.

The present invention provides furthermore a process for the preparation of compounds of formula I which comprises reacting in known manner halo-benzoic acid esters of the formula II

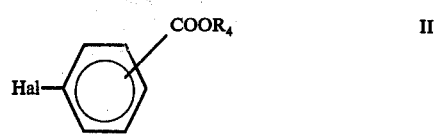

where Hal is halogen, preferably chlorine or bromine, and $R_4$ is alkyl having from 1 to 12, preferably from 1 to 4 carbon atoms, with alkane-phosphonous acid diesters of the formula III $$R_1 - P(OR_5)_2 \quad \text{III}$$

where $R_1$ is as defined above (formula I) and $R_5$ is alkyl having from 1 to 12, preferably from 1 to 4 carbon atoms, at temperatures of from 100° to 250° C and while distilling off the alkyl halide $R_5$-Hal, converting the products obtained and corresponding to the formula Ia

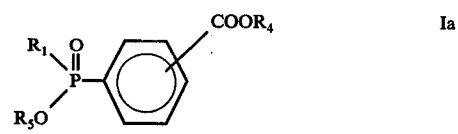

to the corresponding phosphinic and/or benzoic acids, also in known manner, optionally
 (a) by hydrolysis with aqueous acid or lye,
 (b) by ester splitting with gaseous hydrogen chloride,
 (c) by reaction with phosgene, optionally in the presence of N- and/or P-containing catalysts and subsequent hydrolysis of the acid chlorides formed,
and/or optionally esterifying or transesterifying also in known manner the products so obtained with glycols of the formula HO-$(CH_2)_n$-CHR-OH, where $n$ is 1 to 3 and R is hydrogen or alkyl having from 1 to 4 carbon atoms. Also the anhydrides of the carboxyphenyl-alkylphosphinic acids may be prepared.

It is a surprising fact that, for example in contrast to the known process of British Pat. No. 1,200,273 (Example 17, yield 11%), also 2-halo-benzoic acid esters may be converted to the products of the invention with economically interesting yields when alkane-phosphonous acid diesters are used as reactants.

As starting compounds of the formula III there may be used: methanephosphonous acid dimethyl ester, -diethyl ester, -di-isobutyl ester, di-octyl ester, didodecyl ester; ethanephosphonous acid dimethyl ester, -di-isopropyl ester, -dicyclohexyl ester; butanephosphonous acid dimethyl ester, -diethyl ester, -di-isobutyl ester, -di-octyl ester. The preparation of these alkane-phosphonous acid diesters is known.

Suitable starting compounds of the formula II are for example: o-, m-, p-chlorobenzoic acid methyl, -ethyl, -propyl, -butyl, -hexyl, -decyl, -dodecyl ester; o-, m-, p-bromobenzoic acid methyl, -ethyl, -propyl, -butyl, -cyclohexyl, -octyl, -dodecyl ester.

In order to prepare the carboxyphenyl-alkylphosphinic acids, the alkoxycarbonylphenyl-alkylphosphinic acid esters of the invention which can be prepared according to known processes are split off and/or hydrolysed by strong inorganic acids or bases. Examples of these acids are concentrated hydrochloric acid, aqueous sulfuric acid, aqueous phosphoric acid, sodium or potassium hydroxide, calcium, magnesium or barium hydroxide.

Work-up is carried out in known manner. For example, when concentrated hydrochloric acid is used, the water and the hydrogen chloride may be distilled off in a water jet pump vacuum after the reaction is complete, and the remaining crude acid may be recrystallized from water.

Alkali metal salts of the phosphinic acids according to the invention obtained by saponification with alkaline substances may be converted to the phosphinic acids of the invention according to simple known methods.

The ester splitting cited above sub b) may for example be carried out according to the indications given in German Offenlegungsschrift No. 2,156,284, and the phosgenation cited sub c) according to the description of German Offenlegungsschrift No. 2,129,584 and/or 2,321,122.

Compounds of formula I in accordance with the present invention are for example the following:

o-methoxy-carbonyl-phenyl-methylphosphinic acid methyl ester, -ethyl ester, -propyl ester, -butyl ester, -hexyl ester, -octyl ester, -dodecyl ester;

o-methoxy-carbonyl-phenyl-ethylphosphinic acid methyl ester, -ethyl ester, -isopropyl ester, -pentyl ester, -decyl ester;

o-methoxy-carbonyl-phenyl-butyl-phosphinic acid methyl ester, -ethyl ester, -isobutyl ester, -cyclohexyl ester, -dodecyl ester;

o-ethoxy-carbonyl-phenyl-methylphosphinic acid methyl ester, -ethyl ester, -propyl ester, -butyl ester, -hexyl ester, -octyl ester, -dodecyl ester;

o-ethoxy-carbonyl-phenyl-ethylphosphinic acid methyl ester, -ethyl ester, -isopropyl ester, -pentyl ester, -decyl ester;

o-ethoxy-carbonyl-phenyl-butyl-phosphinic acid methyl ester, -ethyl ester, -isobutyl ester, -cyclohexyl ester, -dodecyl ester;

o-butoxy-carbonyl-phenyl-methylphosphinic acid methyl ester, -ethyl ester, -propyl ester, -butyl ester, -hexyl ester, -oxtyl ester, -dodecyl ester;

o-butoxy-carbonyl-phenyl-ethylphosphinic acid methyl ester, -ethyl ester, -isopropyl ester, -pentyl ester, -decyl ester;

o-butoxy-carbonyl-phenyl-butyl-phosphinic acid methyl ester, -ethyl ester, -isobutyl ester, -cyclohexyl ester, -dodecyl ester;

o-hexyloxy-carbonyl-phenyl-methylphosphinic acid methyl ester, -ethyl ester, -propyl ester, -butyl ester, -hexyl ester, -octyl ester, -dodecyl ester;

o-hexyloxy-carbonyl-phenyl-ethylphosphinic acid methyl ester, -ethyl ester, -isopropyl ester, -pentyl ester, -decyl ester;

o-hexyloxy-carbonyl-phenyl-butyl-phosphinic acid methyl ester, -ethyl ester, isobutyl ester, -cyclohexyl ester, -dodecyl ester;

o-dodecyloxy-carbonyl-phenyl-methylphosphinic acid methyl ester, -ethyl ester, -propyl ester, butyl ester, -hexyl ester, -octyl ester, -dodecyl ester;

o-dodecyloxy-carbonyl-phenyl-ethylphosphinic acid methyl ester, -ethyl ester, -isopropyl ester, -pentyl ester, -decyl ester;

o-dodecyloxy-carbonyl-phenyl-butyl-phosphinic acid methyl ester, -ethyl ester, -isobutyl ester, -cyclohexyl ester, -dodecyl ester;

m-methoxy-carbonyl-phenyl-methylphosphinic acid methyl ester, -ethyl ester, -propyl ester, -butyl ester, -cyclohexyl ester, -octyl ester, -decyl ester;

m-methoxy-carbonyl-phenyl-ethylphosphinic acid methyl ester, -ethyl ester, -hexyl ester, -octyl ester, -dodecyl ester;

m-methoxy-carbonyl-phenyl-propylphosphinic acid methyl ester, -ethyl ester, -hexyl ester, -octyl ester, -dodecyl ester;

m-methoxy-carbonyl-phenyl-butyl-phosphinic acid methyl ester, -ethyl ester, -isobutyl ester, -pentyl ester, -heptyl ester, -decyl ester;

m-ethoxy-carbonyl-phenyl-methylphosphinic acid methyl ester, -ethyl ester, -propyl ester, -butyl ester, -cyclohexyl ester, -octyl ester, -decyl ester;

m-ethoxy-carbonyl-phenyl-ethylphosphinic acid methyl ester, -ethyl ester, -hexyl ester, -octyl ester, -dodecyl ester;

m-ethoxy-carbonyl-phenyl-propylphosphinic acid methyl ester, -ethyl ester, -isobutyl ester, -pentyl ester, -heptyl ester, -decyl ester;

m-cyclohexyloxy-carbonyl-phenyl-methylphosphinic acid methyl ester, -ethyl ester, -propyl ester, -butyl ester, -cyclohexyl ester, -octyl ester, -decyl ester;

m-cyclohexyloxy-carbonyl-phenyl-ethylphosphinic acid methyl ester, -ethyl ester, -hexyl ester, -octyl ester, -dodecyl ester;

m-cyclohexyloxy-carbonyl-phenyl-propylphosphinic acid methyl ester, -ethyl ester, -isobutyl ester, -pentyl ester, -heptyl ester, -decyl ester;

m-octyloxy-carbonyl-phenyl-methylphosphinic acid methyl ester, -ethyl ester, -propyl ester, -butyl ester, -cyclohexyl ester, octyl ester, -decyl ester;

m-octyloxy-carbonyl-phenyl-ethylphosphinic acid methyl ester, -ethyl ester, -hexyl ester, -octyl ester, -dodecyl ester;

m-octyloxy-carbonyl-phenyl-propylphosphinic acid methyl ester, -ethyl ester, -isobutyl ester, -pentyl ester, -heptyl ester, -decylester;

p-methoxy-carbonyl-phenyl-methylphosphinic acid methyl ester, -ethyl ester, -propyl ester, -butyl ester, -cyclohexyl ester, -octyl ester, -decyl ester;

p-methoxy-carbonyl-phenyl-ethylphosphinic acid methyl ester, -ethyl ester, -hexyl ester, -octyl ester, -dodecyl ester;

p-methoxy-carbonyl-phenyl-butylphosphinic acid methyl ester, -ethyl ester, -isobutyl ester, -pentyl ester, -heptyl ester, -decyl ester;

p-ethoxy-carbonyl-phenyl-methylphosphinic acid methyl ester, -ethyl ester, -propyl ester, -butyl ester, -cyclohexyl ester, -octyl ester, -decyl ester;

p-ethoxy-carbonyl-phenyl-ethylphosphinic acid methyl ester, -ethyl ester, -hexyl ester, -octyl ester, -dedecyl ester;

p-ethoxy-carbonyl-phenyl-butylphosphinic acid methyl ester, -ethyl ester, isobutyl ester, -pentyl ester, -heptyl ester, -decyl ester;

p-octyloxy-carbonyl-phenyl-methylphosphinic acid methyl ester, -ethyl ester, -propyl ester, -butyl ester, -cyclohexyl ester, -octyl ester, -decyl ester;

p-octyloxy-carbonyl-phenyl-ethylphosphinic acid methyl ester, -ethyl ester, -hexyl ester, -octyl ester, -dodecyl ester;

p-octyloxy-carbonyl-phenyl-butylphosphinic acid methyl ester, -ethyl ester, -isobutyl ester, -pentyl ester, -heptyl ester, -decyl ester;

p-dodecyloxy-carbonyl-phenyl-methylphosphinic acid methyl ester, -ethyl ester, -propyl ester -butyl ester, -cyclohexyl ester, -octyl ester, -decyl ester;

p-dodecyloxy-carbonyl-phenyl-ethylphosphinic acid methyl ester, -ethyl ester, -hexyl ester, -octyl ester, -dodecyl ester;

p-dodecyloxy-carbonyl-phenyl-butylphosphinic acid methyl ester, -ethyl ester, isobutyl ester, -pentyl ester, -heptyl ester, -decyl ester;

as well as the corresponding semi-esters, and furthermore:

o-carboxy-phenyl-methyl-phosphinic acid,
o-carboxy-phenyl-ethyl-phosphinic acid,
o-carboxy-phenyl-butyl-phosohinic acid,
m-carboxy-phenyl-methyl-phosphinic acid,
m-carboxy-phenyl-ethyl-phosphinic acid,
m-carboxy-phenyl-propyl-phosphinic acid,
p-carboxy-phenyl-methyl-phosphinic acid,
p-carboxy-phenyl-ethyl-phosphinic acid,
p-carboxy-phenyl-butyl-phosphinic acid,
o-carboxy-phenyl-methylphosphinic acid-diglycolic ester,
-dipropylene-glycolic ester, -di-(1,4-butanediol) ester;
o-carboxy-phenyl-ethylphosphinic acid-diglycolic ester, -dipropylene-glycolic ester,-di-(1,3-butanediol) ester;
o-carboxy-phenyl-butylphosphinic acid-diglycolic ester, -dipropyleneglycolic ester, -di-(1,4-butanediol) ester, m-carboxy-phenyl-methylphosphinic acid-diglycolic ester, -dipropylene-glycolic ester, -di-(1,4-butanediol) ester;
m-carboxy-phenyl-ethylphosphinic acid-diglycolic ester, -dipropylene-glycolic ester, -di-(1,3-butanediol) ester;
m-carboxy-phenyl-propylphosphinic acid-diglycolic ester, -dipropylene-glycolic ester, -di-(1,4-butanediol) ester;
p-carboxy-phenyl-methylphosphinic acid diglycolic ester, -dipropylene-glycolic ester, -di-(1,4-butanediol) ester, p-carboxy-phenyl-ethylphosphinic acid-diglycolic ester, -dipropylene-glycolic ester, -di-(1,3-butanediol) ester;
p-carboxyl-phenyl-butylphosphinic acid-diglycolic ester, dipropylene-glycolic ester, -di-(1,4-butanediol) ester.

The compounds of the invention are interesting intermediate products, for example for the manufacture of plant protecting agents and pharmaceuticals. They may also be used advantageously as valuable corrosion inhibitors and complexing agents. They are used, however, especially as comonomers for the preparation of plastics, for example polymers, polycondensates, or polyaddition products, for example polyesters, especially linear ones, such as terephthalic acid polyesters, to which they impart good flame-repellent properties, but especially an improved dyeability. As compared to the hitherto known organo-phosphorus compounds, such as triphenylphosphine oxide, which may be added to polyesters, the compounds of the invention have the advantage of providing better thermostablity and lower volatility.

The following examples illustrate the invention.

EXAMPLE 1

(a) Preparation of o-ethoxycarbonylphenyl-methyl-phosphinic acid ethyl ester.

91 g of bromobenzoic acid ethyl ester and 3 g of nickel chloride are heated to 190° C and, with vigorous agitation, 54 g of methanephosphonous acid diethyl ester are added dropwise within 4 hours, and the ethyl bromide formed is distilled off. After complete reaction, distillation is carried out. 67 g of o-ethoxycarbonylphenyl-methylphosphinic acid ethyl ester having a boiling point at 0.6 torr of 139°–144° C are obtained, which corresponds to a yield of 66% of the theoretical yield.

(b) Preparation of o-carboxyphenyl-methylphosphinic acid.

200 ml of concentrated hydrochloric acid are added to 106 g of o-ethoxycarbonylphenyl-methylphosphinic acid ethyl ester and the reaction mixture is refluxed while simultaneously a hydrogen chloride current is slowly passed through. After 24 hours, the water and the hydrogen chloride are distilled off. The residue is dried over potassium hydroxide. 78 g of o-carboxyphenyl-methylphosphinic acid having a melting point of 170°–172° C (recrystallized from water) are obtained, which corresponds to a yield of 95%.

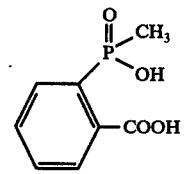

EXAMPLE 2

(a) Preparation of m-ethoxycarbonylphenyl-methylphosphinic acid ethyl ester.

Under a nitrogen atmosphere, 100 g of m-chlorobenzoic acid ethyl ester and 3 g of nickel chloride are heated to 200°–210° C and, with vigorous agitation, 73 g of methanephosphonous acid-diethyl ester are added dropwise within 2 hours, and the ethyl chloride formed is distilled off. Distillation is carried out after the reaction is complete. 89 g of m-ethoxycarbonylphenylmethylphosphinic acid ethyl ester having a boiling point at 0.7 torr of 140°–145° C are obtained, corresponding to a yield of 64%.

(b) Preparation of m-carboxyphenyl-methylphosphinic acid.

200 ml of concentrated hydrochloric acid are mixed with 130 g of m-ethoxycarbonylphenyl-methylphosphinic acid-ethyl ester, and the mixture is maintained for 7 hours at 100° C, while simultaneously a hydrogen chloride current is slowly passed through the reaction mixture. Subsequently, the mixture is cooled and suction-filtered. After drying over potassium hydroxide, 80 g of m-carboxyphenyl-methylphosphinic acid having a melting point of 230°–232° C (recrystallized from water) are obtained, which corresponds to a yield of 80%.

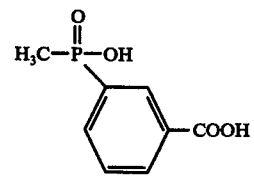

EXAMPLE 3

(a) Preparation of p-ethoxycarbonylphenyl-methylphosphinic acid ethyl ester.

405 g of p-bromobenzoic acid ethyl ester and 12 g of nickel chloride are heated to 170°–180° C, and, with vigorous agitation, 240 g of methanephosphonous acid-diethyl ester are added dropwise within 3 hours, the ethyl bromide formed being distilled off. Distillation is carried out after the reaction is complete. 355 g of p-ethoxycarbonylphenyl-methylphosphinic acid-ethyl ester having a boiling point at 0.6 torr of 148°–150° C are obtained, which corresponds to a yield of 78%.

(b) Preparation of p-carboxylphenyl-methylphosphinic acid.

200 g of p-ethoxycarbonylphenyl-methylphosphinic acid ethyl ester are refluxed with concentrated hydrochloric acid in excess. After the reaction is complete, the water and the hydrogen chloride are distilled off in a water jet pump vacuum. The residue is recrystallized from water. 135 g of p-carboxyphenyl-methylphosphinic acid having a melting point of 238° C to 240° C are obtained, corresponding to a yield of 87%.

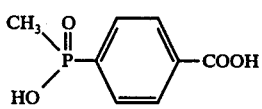

What is claimed is:

1. A carboxyphenyl-alkylphosphinic acid of the formula

wherein $R_1$ is alkyl of 1 to 4 carbon atoms, $R_3$ is hydrogen, alkyl of from 1 to 12 carbon atoms or hydroxyalkyl having the formula HO—$(CH_2)_n$-CHR—, $n$ is 1 to 3 and R is hydrogen or alkyl of 1 to 4 carbon atoms.

2. A compound as defined in claim 1 wherein $R_3$ is hydrogen.

3. The compound defined in claim 1 which is o-carboxylphenyl-methylphosphinic acid.

4. The compound defined in claim 1 which is m-carboxyphenyl-methylphosphinic acid.

5. The compound defined in claim 1 which is p-carboxyphenyl-methylphosphinic acid.

* * * * *